United States Patent [19]

Harnish et al.

[11] B 3,998,951
[45] Dec. 21, 1976

[54] SUBSTITUTED 2-ARYLQUINAZOLINES AS FUNGICIDES

[75] Inventors: Wayne Nelson Harnish, Medina; Arthur Albert Ramsey, Middleport, both of N.Y.

[73] Assignee: FMC Corporation, Philadelphia, Pa.

[22] Filed: Mar. 13, 1974

[21] Appl. No.: 450,870

[44] Published under the second Trial Voluntary Protest Program on March 16, 1976 as document No. B 450,870.

[52] U.S. Cl. ............................ 424/251; 260/251 Q
[51] Int. Cl.² ............................................. A01N 9/22
[58] Field of Search ............... 424/251; 260/251 Q, 260/251 QA

[56] References Cited
UNITED STATES PATENTS

| 1,880,447 | 10/1932 | Hentrich et al. | 260/251 QA |
| 3,755,582 | 8/1973 | Bullock | 424/251 |

OTHER PUBLICATIONS

Chemical Abstracts, vol. 55 (1961), p. 1009h.
Chemical Abstracts, vol. 76 (1972), p. 149497u.

*Primary Examiner*—V. D. Turner

[57] ABSTRACT

Fungicidal compositions based on substituted 2-arylquinazolines exhibit antifungal activity particularly against rusts and mildews. The synthesis of new compounds is described and the utility of antifungal compositions is exemplified.

13 Claims, No Drawings

SUBSTITUTED 2-ARYLQUINAZOLINES AS FUNGICIDES

This invention pertains to the general field of fungicides, particularly to agricultural fungicides useful in the control of rusts and mildews.

The required quinazolinones are prepared from readily obtainable raw materials employing the known reaction of 2-aminobenzamide (anthranilamide) (IV) with aromatic acyl chloride to form an acylamidobenzamide (III), and cyclizing this intermediate to a 2-arylquinazolinone (II):

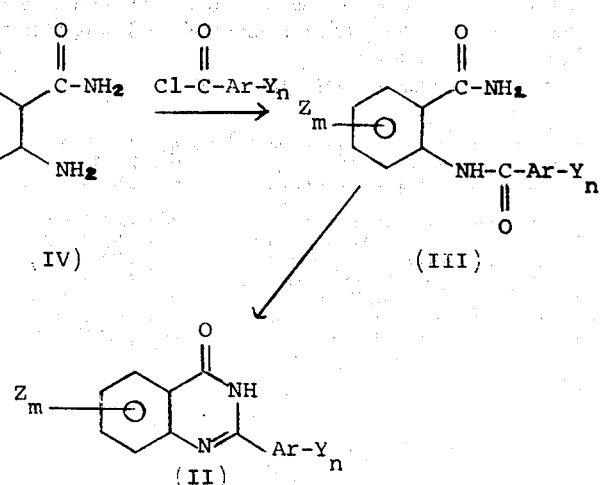

Certain 2-aryl-4-haloquinazolines have been described in the literature, but no reference has been found which suggests the outstanding antifungal activity of the active compounds of the present invention.

Fungicidal activity is exhibited by compositions comprising as an active ingredient one or more compounds of the general formula:

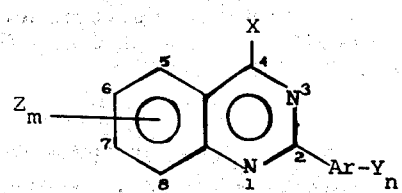

wherein Ar is phenyl, thienyl, furyl or other heterocyclyl group; X is chlorine, bromine or mercapto radical; Y and Z may be the same or different and may be halogen, alkyl, alkoxy, alkylthio or dialkylamino, in each of which the alkyl group may contain 1 to 4 carbon atoms, trifluoromethyl or phenyl; and $m$ and $n$ are each 0, 1 or 2.

In the preferred embodiments of the present invention, X is chlorine or bromine, Y is halogen or alkyl, Z is alkyl, and $m$ and $n$ are each 0 or 1.

The active ingredients of the present invention are 2-arylquinazolines (I) prepared from the corresponding 2-arylquinazolinones (II):

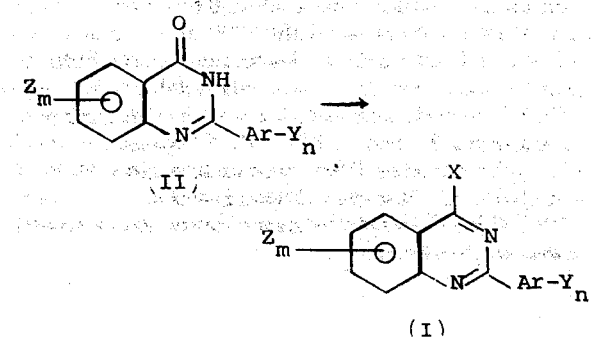

An alternative method of obtaining the 2-arylquinazolinones is illustrated in Example III. This starts with reaction between 2-aminobenzoic acid (anthranilic acid) and an aromatic acid anhydride, and the resulting product is reacted with formamide to yield II.

The preparation of representative antifungal compounds of the invention and illustration of their antifungal properties are set forth in the following examples. All proportions in the examples and the specification are by weight unless otherwise indicated. All temperatures are in degrees centigrade. All reduced pressures not otherwise designated are the pressures normally attainable using a water aspirator.

Following the method of Weidinger and Wellenreuther (Chem. Abstracts 60, 2987–2988 (1944)), the acylamidobenzamide (III) intermediates were prepared as below:

To a stirred mixture of 16.3 g of 2-aminobenzamide, 82 ml of saturated aqueous sodium acetate solution and 82 ml of acetic acid was added a solution of 21 g of 4-chlorobenzoyl chloride in 14 ml of acetone. The mixture was stirred at room temperature for one hour after addition was complete. The tan precipitate was collected by filtration and recrystallized from ethanol to give 24.1 g of light tan 2-(4-chlorobenzamido)benzamide, m.p. 205°–207°, which was used without further purification.

In a similar manner were prepared:

| | |
|---|---|
| 2-benzamidobenzamide, | m.p. 218°–220° |
| 2-(4-methylbenzamido)benzamide, | m.p. 211°–213° |
| 2-(4-tert-butylbenzamido)benzamide, | m.p. 184°–186° |
| 2-(2-chlorobenzamido)benzamide, | m.p. 202°–203° |
| 2-(3-chlorobenzamido)benzamide, | m.p. 186°–187° |
| 2-(4-ethylbenzamido)benzamide, | m.p. 192.5°–194° |
| 2-(4-ethoxybenzamido)benzamide, | m.p. 201°–203° |
| 2-(thienyl-2-carboxamido)benzamide, | m.p. 185°–186° |
| 2-(2-methylbenzamido)benzamide, | m.p. 218°–220° |
| 2-(2-furamido)benzamide, | m.p. 241° |

Treatment of the acylamidobenzamide with sodium hydroxide in pyridine caused ring closure to yield the intermediate 2-arylquinazolin-4(3H)-one as exemplified below:

A mixture of 11 ml of pyridine in 340 ml of 2 normal aqueous sodium hydroxide was heated to the reflux temperature and to the hot solution was added in one portion 16.3 g of 2-(4-methylbenzamido)benzamide. The mixture was maintained at reflux temperature for 15 minutes, then poured into 1000 ml of ice. The cold mixture was acidified with concentrated hydrochloric acid and the precipitate was cooled to give 14.1 g of white 2-(4-methylphenyl)-quinazolin-4(3H)-one, m.p. 242°–243.5° (from ethanol).

In a similar manner were prepared:

| | |
|---|---|
| 2-(4-chlorophenyl)quinazolin-4(3H)-one, | m.p. 308°–310° |
| 2-phenylquinazolin-4(3H)-one, | m.p. 238.5°–240° |
| 2-(4-tert-butylphenyl)quinazolin-4(3H)-one, | m.p. 226°–227° |
| 2-(2-chlorophenyl)quinazolin-4(3H)-one, | m.p. 184°–185.5° |
| 2-(3-chlorophenyl)quinazolin-4(3H)-one, | m.p. 296°–297.5° |
| 2-(4-ethylphenyl)quinazolin-4(3H)-one, | m.p. 229°–230° |
| 2-(4-ethoxyphenyl)quinazolin-4(3H)-one, | m.p. 250°–252° |
| 2-(2-thienyl)quinazolin-4(3H)-one, | m.p. 283°–284° |
| 2-(2-methylphenyl)quinazolin-4(3H)-one, | m.p. 218°–220° |
| 2-(2-furyl)quinazolin-4(3H)-one, | m.p. 221°–221.5° |

EXAMPLE I

4-Chloro-2-(4-methylphenyl)quinazoline

To a mixture of 7 g of 2-(4-methylphenyl)quinazolin-4(3H)-one and 50 ml of thionyl chloride was slowly added 2.16 g of dimethylformamide and the mixture was heated under reflux for 75 minutes. The mixture was poured into 250 ml of ice and the ice allowed to melt. The precipitate was collected to give 6.7 g of 4-chloro-2-(4-methylphenyl)quinazoline which melted at 113°–115° after recrystallization from petroleum ether (30°–60° fraction); ir and nmr spectra were consistent with the assigned structure. Calcd. for $C_{15}H_{11}ClN_2$: C, 70.73; H, 4.35; N, 11.00. Found: C, 70.92; H, 4.39; N, 11.09.

EXAMPLE II

4-Chloro-2-phenylquinazoline

To a mixture of 20.8 g of 2-phenylquinazolin-4(3H)-one and 195 ml of thionyl chloride was slowly added 6.85 g of dimethylformamide and the mixture was heated under reflux for 75 minutes. The mixture was poured into 1000 ml of ice and the ice allowed to melt. The precipitate was collected by filtration to give a tan solid, m.p. 135°. The still-moist solid was dissolved in methylene chloride, the solution was dried over magnesium sulfate and was filtered. The filtrate was evaporated to dryness and the residue recrystallized from hexane to give 10.45 g of 4-chloro-2-phenylquinazoline which melted at 127°–128.5°.

EXAMPLE III

4-Chloro-6-methyl-2-phenylquinazoline

A mixture of 15 g of benzoic anhydride and 10.02 g of 5-methylanthranilic acid was heated at 90° for 3 hours. The solid mass was dissolved in boiling 10% aqueous potassium hydroxide. The solution was acidified with dilute hydrochloric acid and the precipitate collected by filtration to give solid 2-benzamido-5-methylbenzoic acid, m.p. 205°–208°.

A mixture of 9.3 g of 2-benzamido-5-methylbenzoic acid and 2.6 g of formamide was heated at 155°–180° for three hours. The solid mass was dissolved in hot 5% potassium hydroxide solution. The solution was acidified with hydrochloric acid and the precipitate collected on a filter. The solid was triturated with aqueous sodium bicarbonate solution and the washed solid was recrystallized from a mixture of dimethylformamide and water to give, after drying, 2.1 g of 6-methyl-2-phenylquinazolin-4(3H)-one, m.p. 258°–260.5°.

To a stirred slurry of 2.1 g of 6-methyl-2-phenylquinazolin-4(3H)-one and 35 ml of thionyl chloride was added dropwise 1.3 g of dimethylformamide. The mixture was maintained at reflux temperature for 90 minutes. The mixture was concentrated under reduced pressure, the residual solid was mixed with crushed ice and the washed solid collected. Two recrystallizations from petroleum ether (60°–110° fraction) gave 1.5 g of 4-chloro-6-methyl-2-phenylquinazoline, m.p. 111°–113°.

EXAMPLE IV

4-Chloro-2-(4-chlorophenyl)quinazoline

To a mixture of 15.8 g of 2-(4-chlorophenyl)quinazolin-4(3H)-one and 115 ml of thionyl chloride was added dropwise 4.5 g of dimethylformamide and the mixture was treated as described in Example I to obtain a yellow solid which was recrystallized from cyclohexane to give 13.6 g of light yellow 4-chloro-2-(4-chlorophenyl)quinazoline, m.p. 166°–167°; ir and nmr spectra were consistent with the assigned structure.

Calcd. for $C_{14}H_8Cl_2N_2$: C, 61.12; H, 2.93; N, 10.18. Found: C, 61.41; H, 3.05; N, 10.14.

EXAMPLE V

4-Chloro-2-(3-chlorophenyl)quinazoline

A mixture of 5.5 g of 2-(3-chlorophenyl)quinazolin-4(3H)-one and 40 ml of thionyl chloride was treated as described in Example I with 1.57 g of dimethylformamide to give, after recrystallization from cyclohexane, 4.4 g of white 4-chloro-2-(3-chlorophenyl)quinazoline, m.p. 157°–158.5°.

Calcd. for $C_{14}H_8Cl_2N_2$: C, 61.12; H, 2.93; N, 10.18. Found: C, 61.10; H, 2.88; N, 10.32.

EXAMPLE VI

4-Chloro-2-(2-chlorophenyl)quinazoline

A mixture of 17.5 g of 2-(2-chlorophenyl)quinazolin-4(3H)-one and 130 ml of thionyl chloride was treated as described in Example I with 5 g of dimethylformamide. The mixture was poured into 1000 ml of ice water and stirred until the ice was melted. The solid was collected by filtration and allowed to air-dry overnight. The solid was triturated with 500 ml of boiling cyclohexane. The insoluble solid was removed by filtration and the cyclohexane solution allowed to cool slowly. The solid which separated was collected to give pale yellow needles, m.p. 127°–129°. Recrystallization of the yellow needles from cyclohexane gave 9.9 g of 4-chloro-2-(2-chlorophenyl)quinazoline, m.p. 129.5°–130.5°; ir and nmr spectra were consistent with the assigned structure.

Calcd. for $C_{14}H_8Cl_2N_2$: C, 61.12; H, 2.93; N, 10.18. Found: C, 61.00; H, 3.00; N, 10.36.

EXAMPLE VII

4-Chloro-2-(4-*tert*-butylphenyl)quinazoline

A mixture of 8.9 g of 2-(4-*tert*-butylphenyl)quinazolin-4(3H)-one and 60 ml of thionyl chloride was treated with 2.34 g of dimethylformamide as described in Example VI. The initial solid was triturated with cyclohexane, filtered, and the filtrate concentrated to give an oil which solidified on standing to give a solid, m.p. 74°–77°. This solid was recrystallized twice from petroleum ether (30°–60° fraction) using a low-temperature recrystallization apparatus to give 6.3 g of 4-chloro-2-(4-*tert*-butylphenyl)quinazoline, m.p. 75°–76.5°; ir and nmr spectra were consistent with the assigned structure.

Calcd. for $C_{18}H_{17}ClN_2$: C, 72.84; H, 5.77; N, 9.44. Found: C, 72.65; H, 6.06; N, 9.31.

EXAMPLE VIII

4-Chloro-2-(2-thienyl)quinazoline

To a stirred suspension of 22.8 g of 2-(2-thienyl)-quinazolin-4(3H)-one in 200 ml of thionyl chloride was added in small quantities 7.3 g of dimethylformamide. The mixture was stirred for 2 hours, then poured into 2 liters of ice. The yellow solid was recrystallized three times from cyclohexane to give 16.7 g of 4-chloro-2-(2-thienyl)-quinazoline, m.p. 121.5°–123°; ir and nmr spectra were consistent with the assigned structure.

Calcd. for $C_{12}H_7ClN_2S$: C, 58.42; H, 2.85; N, 11.35. Found: C, 58.21; H, 3.05; N, 11.45.

EXAMPLE IX

4-Chloro-2-(4-ethylphenyl)quinazoline

A mixture of 7.43 g of 2-(4-ethylphenyl)quinazolin-4(3H)-one and 50 ml of thionyl chloride was treated with 2.17 g of dimethylformamide as described in Example I. The solid was recrystallized twice from petroleum ether (60°–110° fraction) to give 4.23 g of light-colored 4-chloro-2-(4-ethylphenyl)quinazoline, m.p. 75.5°–76.5°; ir and nmr spectra were consistent with the assigned structure.

Calcd. for $C_{16}H_{13}ClN_2$: C, 71.51; H, 4.88; N, 10.42. Found: C, 71.60; H, 5.00; N, 10.48.

EXAMPLE X

4-Chloro-2-(2-methylphenyl)quinazoline

A mixture of 7.6 g of 2-(2-methylphenyl)quinazolin-4(3H)-one and 55 ml of thionyl chloride was treated with 2.35 g of dimethylformamide as described in Example I. The isolated solid was recrystallized from cyclohexane to give 5.1 g of 4-chloro-2-(2-methylphenyl)quinazoline, m.p. 103°–104°; ir and nmr spectra were consistent with the assigned structure.

Calcd. for $C_{15}H_{11}ClN_2$: C, 70.70; H, 4.35; N, 11.00. Found: C, 70.59; H, 4.62; N, 10.72.

EXAMPLE XI

4-Chloro-2-(2-furyl)quinazoline

A 2.12 g portion of 2-(2-furyl)quinazolin-4(3H)-one was stirred into 25 ml of phosphorus oxychloride and to this mixture was slowly added 1.21 g of dimethylaniline. This mixture was stirred for 15 minutes. The entire mixture was added slowly to 1 liter of cold water containing 25 ml of chloroform. Solid sodium bicarbonate was added as required to keep the water solution basic. The chloroform extract was separated and the water extracted with an additional 25 ml of chloroform. The chloroform extracts were combined and concentrated to give a yellow solid. The solid was recrystallized from cyclohexane to give 1.4 g of 4-chloro-2-(2-furyl)-quinazoline, m.p. 116°–118°; ir and nmr spectra were consistent with the assigned structure.

Calcd. for $C_{12}H_7ClN_2O$: C, 62.30; H, 3.27; N, 12.17. Found: C, 62.62; H, 3.21; N, 12.22.

EXAMPLE XII

4-Chloro-2-(4-ethoxyphenyl)quinazoline

A mixture of 16.65 g of 2-(4-ethoxyphenyl)quinazolin-4(3H)-one and 130 ml of thionyl chloride was treated with 4.57 g of dimethylformamide as described in Example I. The isolated solid was dissolved in methylene chloride, the solution dried over magnesium sulfate and a dried solution concentrated. The yellow solid was recrystallized from petroleum ether (60°–110° fraction), but was found by thin-layer chromatography to contain an impurity. The solid was purified by column chromatography using a silica gel column with a 1:1 mixture of benzene and cyclohexane as the eluting solvent. The first 350 ml (fractions 1 and 2) collected were devoid of compound; the next 15 fractions (50 ml each) were found by thin-layer chromatography to contain two components. Fraction 18 was found by thin-layer chromatography to consist of a single compound. Fourteen 50-ml fractions of eluent were collected and concentrated to give 2.67 g of white solid, m.p. 118°–120°; nmr analysis showed this to be the desired 4-chloro-2-(4-ethoxyphenyl)quinazoline.

Calcd. for $C_{16}H_{13}ClN_2O$: C, 67.49; H, 4.60; N, 9.84. Found: C, 67.26; H, 4.87; N, 9.78.

EXAMPLE XIII

4-Bromo-2-phenylquinazoline

Into a mixture of 5 g of 2-phenylquinazolin-4(3H)-one and 1.82 g of triethylamine in 100 ml of toluene was added a solution of 25.8 g of phosphorus oxybromide in 50 ml of toluene. The mixture was warmed slightly and the insoluble quinazolinone dissolved slowly, with a new solid appearing. The reaction mixture was heated at 80°–85° for approximately 24 hours. The reaction mixture was cooled and the solid which separated was collected on a filter. The collected solid was dissolved in chloroform, was washed twice with 100-ml portions of water and the washed solution dried over magnesium sulfate. The solution was concentrated to dryness to leave a light orange solid, m.p. 131°–132°. This solid was recrystallized from cyclohexane to give 2.97 g of light yellow 4-bromo-2-phenylquinazoline, m.p. 131.5°–132.5°; ir and nmr spectra were consistent with the assigned structure.

EXAMPLE XIV

4-Mercapto-2-phenylquinazoline

A solution of potassium hydrosulfide was prepared by bubbling 4.24 g of hydrogen sulfide gas into a solution of 6.99 g of potassium hydroxide in 80 ml of ethanol. To this solution was added in small portions 15 g of 4-chloro-2-phenylquinazoline. When addition was complete, the mixture was heated at 65° for one hour. (During this heating period, a small amount of concentrated aqueous sodium hydroxide entered the reaction vessel inadvertently when the gas trap was "backed up".) The reaction mixture was acidified with 2 normal hydrochloric acid. The yellow solid was collected and recrystallized twice from ethanol to give 10.28 g of fine yellow needles of 4-mercapto-2-phenylquinazoline, m.p. 222°–224°; ir and nmr spectra were consistent with the assigned structure.

Calcd. for $C_{14}H_{10}N_2S$: C, 70.56; H, 4.23; N, 11.76. Found: C, 70.61; H, 4.31; N, 11.84.

EXAMPLE XV

Biological Tests

A 25% wettable powder (25 WP) formulation was prepared by grinding together 250 parts of the substituted 2-arylquinazoline, 720 parts of attapulgite clay, 15 parts of sodium lignosulfonate and 15 parts of sodium alkylnaphthalenesulfonate.

A continually stirred suspension of 210 mg of a 25 WP formulation in 350 ml of water, equivalent to 150 ppm of active ingredient, was applied to bean plants (*Phaseolus vulgaris* - 10 to 12 days old; primary-leaf stage), to cucumber plants (*Cucumis sativus* - second true leaf emerging), and to rice plants (*Oryza sativa* - 2- to 3-leaf stage; about 25 plants per pot) by means of stationary atomizing nozzles operating under 20 psi air pressure and situated such that one nozzle was directed above and one below the foliage of the plant. During spraying, the plant being treated was rotated on a turntable such that all parts of the plant were wet to run-off. The treated plants were set aside to dry.

A. Activity Against Bean Powdery Mildew

The day after chemical treatment, a set of two bean plants was inoculated with *Erysiphe polygoni*, the causal agent of bean powdery mildew. A plant carrying a mature infection of the mildew was shaken above the test plants to enable a cloud of conidia of the mildew organism to settle onto the upper surfaces of the leaves of the test plants. The test plants were held in the greenhouse under normal growing conditions and observed (4 to 10 days) until disease symptoms had developed on plants inoculated as above but which had received no chemical treatment. The percent reduction in disease incidence resulting from the chemical treatment was recorded. Results of the tests are summarized in Table I.

B. Activity Against Bean Rust

The day after chemical treatment, a set of two bean plants was inoculated by shaking above it a dust containing 2% by weight in a talc of the urediospores of *Uromyces phaseoli* (causal organism of bean rust). The inoculated plants were transferred to a growth chamber and maintained at 20°–23° and 100% relative humidity for 24 hours, then were transferred to the greenhouse where they were maintained under normal growing conditions until disease symptoms had developed on inoculated but chemically untreated plants, usually 4 to 6 days. The percent reduction in disease incidence resulting from the chemical treatment was recorded. Results are summarized in Table I.

C. Activity Against Rice Blast

The day after chemical treatment, a set of two pots of rice plants was inoculated with *Pyricularia oryzae*, causal organism of rice blast. The test plants were sprayed to run-off with a suspension in distilled water of spores of the causal agent (125,000–150,000 spores/ml), using the same equipment as for the chemical treatment. The inoculated plants were transferred to a growth chamber where they were maintained at 20–23° and 100% relative humidity for 24 hours, then were transferred to the greenhouse and maintained and observed as described in A and B above. Results are summarized in Table I.

D. Activity Against Angular Leaf Spot

The day after chemical treatment, a set of two cucumber plants was inoculated by spraying to run-off with a suspension of *Pseudomonas lachrymans*, causal agent of angular leaf spot. The water suspension contained 125,000 bacterial cells/ml and 5% (w/v) of silicon carbide particles (250-mesh), and was sprayed from the same equipment as that utilized for the chemical treatment, but operated under 40 psi air pressure. The inoculated plants were transferred directly to the greenhouse where they were maintained and observed as described in A and B above. Results are summarized in Table I.

Table I

Percent Reduction in Disease Incidence
(Plants sprayed to run-off with solution containing 150 ppm of active compound)

| Compound of Example | Bean Powdery Mildew | Bean Rust | Rice Blast | Angular Leaf Spot |
| --- | --- | --- | --- | --- |
| I | 0 | 90 | 0 | 0 |
| II | 100 | 98 | 0 | 0 |
| III | 95 | 0 | 0 | — |
| IV | 100 | 75 | 0 | 90 |
| V | 100 | 0 | 0 | 0 |
| VI | 0 | 0 | 0 | 0 |
| VII | 100 | 50 | 0 | 0 |
| VIII | 100 | 100 | 0 | 0 |
| IX | 0 | 75 | 0 | 90 |
| X | 100 | 0 | 95 | 85 |
| XI | 0 | 98 | 90 | 0 |
| XII | 100 | 83 | 0 | 0 |
| XIII | 100 | 100 | 0 | 0 |
| XIV | 0 | 0 | 100 | 0 |

EXAMPLE XVI

Evaluation of Biological Activity

Bean plants and cucumber plants were treated, inoculated and maintained as described in Example XV, using suspensions of the 25% wettable powder formulations corresponding to varying concentrations of active ingredient (160 mg of formulation in 500 ml of water corresponds to 80 ppm of active ingredient). *Erysiphe cichoracearum*, the causal agent of cucumber mildew, was applied to cucumber plants in the same manner as *E. polygoni* was applied to bean plants. Results of these tests are summarized in Table II.

Table II

Evaluation of Fungicidal Activity
Percent Reduction in Disease Incidence

| Compound of Example | ppm applied | Bean Powdery Mildew | Cucumber Mildew | Bean Rust |
| --- | --- | --- | --- | --- |
| I | 80 | 85 | 76 | 8 |
|   | 40 | 24 | 0 | 8 |
|   | 20 | 9 | 38 | 3 |
|   | 10 | 2 | 11 | 1 |
| II | 80 | 79 | 38 | 92 |
|   | 40 | 7 | 11 | 85 |
|   | 20 | 24 | 0 | 32 |
|   | 10 | 0 | 38 | 8 |
| III | 150 | 95 | 92 | — |
|   | 75 | 92 | 58 | — |
| IV | 80 | 33 | 82 | 70 |
|   | 40 | 24 | 38 | 32 |
|   | 20 | 4 | 38 | 3 |
|   | 10 | 37 | 22 | 3 |
| V | 80 | 59 | 76 | 32 |
|   | 40 | 70 | 11 | 1 |
|   | 20 | 47 | 11 | 18 |
|   | 10 | 4 | 0 | 0 |

Table II-continued

Evaluation of Fungicidal Activity  
Percent Reduction in Disease Incidence

| Compound of Example | ppm applied | Bean Powdery Mildew | Cucumber Mildew | Bean Rust |
|---|---|---|---|---|
| VI | 160 | 97 | 76 | 94 |
|  | 80 | 94 | 49 | 85 |
|  | 40 | 33 | 82 | 59 |
| VII | 80 | 90 | 4 | 22 |
|  | 40 | 47 | 22 | 13 |
|  | 20 | 47 | 11 | 1 |
|  | 10 | 4 | 0 | 1 |
| VIII | 160 | 94 | 91 | 95 |
|  | 80 | 87 | 71 | 90 |
|  | 40 | 90 | 71 | 85 |
| IX | 160 | 85 | 88 | 85 |
|  | 80 | 70 | 65 | 85 |
|  | 40 | 24 | 65 | 13 |
| XII | 160 | 95 | 76 | 46 |
|  | 80 | 78 | 53 | 22 |
|  | 40 | 59 | 11 | 22 |
| XIII | 160 | 98 | 76 | 97 |
|  | 80 | 87 | 53 | 92 |
|  | 40 | 47 | 65 | 70 |

Results obtained in tests at different times are recorded in Table I, while the results in Table II were obtained in tests which were all run at the same time (except for the compound of Example III). The variations in results between some tests in the two tables are typical of results obtained in the evaluation of biological activity.

At the concentrations which were tested, the compounds generally did not show systemic activity against test organisms, and were not active in soil incorporation tests. The compounds were relatively inactive in foliar applications against late and early blights and against bacterial spot at the levels tested.

The effective fungicidal compositions of this invention are obtained when substituted 2-arylguinazolines are formulated with any of the relatively inert adjuvants and carriers normally employed for facilitating the dispersion of active ingredients for antifungal applications, recognizing the fact that the formulation and mode of application of a toxicant may affect the activity of the material in a given application. If the formulation permits even distribution of the active ingredients and provides contact with the area to be protected or disinfected, the precise nature of the formulation is not critical. Thus the quinazolines may be formulated as wettable powders, as dusts, as emulsifiable concentrates, as solutions, or as any of several other known types of formulations, depending on the desired mode of application. These formulations may contain as little as 0.5% to as much as 95% or more by weight of active ingredient.

Wettable powders are in the form of finely divided particles which disperse readily in water or other dispersant. The wettable powder is ultimately applied either as a dry powder or as a suspension in water or other liquid. Typical carriers for wettable powders include fuller's earth, kaolin clays, silicas or other readily wet organic or inorganic diluents. Wettable powders normally are prepared to contain about 5 to 95% of active ingredient, depending on the absorbency of the carrier, and usually also contain a small amount of a wetting or dispersing agent. For example, a useful wettable powder formulation contains 25.0 parts of 4-chloro-2-phenylquinazoline, 72.0 parts of attapulgite clay, and 1.5 parts of sodium lignosulfonate and 1.5 parts of sodium alkylnaphthalenesulfonate as wetting agents.

Dusts are free-flowing admixtures of the active ingredient with finely divided solids such as talc, natural clays, kieselguhr, flours such as walnut shell and cotton seed flours, and other organic and inorganic solids which act as dispersants and carriers for the toxicant; these finely divided solids have an average particle size of less than about 50 microns. A typical dust formulation, useful herein, is one containing 1.0 part of 4-chloro-2-(4-methylphenyl)quinazoline and 99.0 parts of talc.

Emulsifiable concentrates are homogeneous liquid or paste compositions which are dispersible in water or other dispersant, and may consist entirely of the substituted quniazoline with a liquid or solid emulsifying agent, or may also contain a liquid carrier, such as xylene, heavy aromatic naphthas, dimethyl sulfoxide, isophorone, and other nonvolatile organic solvents. For application, these concentrates are dispersed in water or other liquid carrier, and normally applied as a spray to the area to be treated. The percentage by weight of the essential active ingredient may vary according to the manner in which the composition is to be applied, but in general comprises 0.5 to 95% of the antifungal composition.

Other useful formulations for antifungal applications include simple solutions of the active ingredient in dispersant in which it is completely soluble at the desired concentration, such as acetone, alkylated naphthalenes, xylene, or other organic solvents.

Typical wetting, dispersing, or emulsifying agents used in agricultural formulations include, for example, the alkyl and alkylaryl sulfonates and sulfates and their sodium salts; and other types of surface-active agents, many of which are available in commerce. The surface-active agent, when used, normally comprises from 1 to 15% by weight of the composition.

These formulations may be applied without further dilution or as dilute solutions, emulsions or suspensions in water or other suitable diluent. The compositions may be applied to the area where control is desired by spraying onto the vegetation it is desired to protect in the case of liquid compositions, or by distribution from mechanical equipment in the case of solids.

The active antifungal compositions of this invention may be formulated or applied with insecticides, nematicides, herbicides, plant growth regulators, fertilizers and other agricultural chemicals. In applying the antifungal compositions of this invention, whether alone or with other agricultural chemicals, an effective amount and concentration of the active ingredient 2-arylquinazoline are of course employed.

It is apparent that modifications may be made in the formulation and application of the compositions of this invention, without departing from the novel concept as defined in the following claims.

We claim:

1. A fungicidal composition which comprises, as active ingredient, a fungicidally effective amount of a quinazoline of the formula:

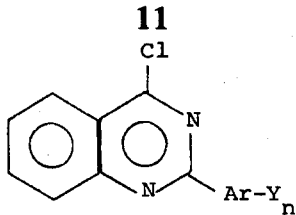

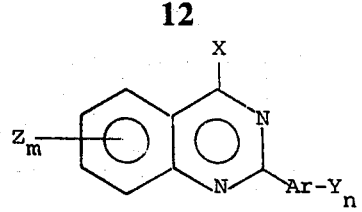

wherein Ar is phenyl or thienyl; Y is halogen or alkyl of 1 to 4 carbons; and $n$ is 0 or 1; with the proviso that when Ar is phenyl and Y is chlorine, Y is in the 3- or 4-position of the phenyl ring; in admixture with an agriculturally acceptable carrier, and a surface-active agent.

2. The fungicidal composition of claim 1 wherein the compound is 4-chloro-2-(4-methylphenyl)quinazoline.

3. The fungicidal composition of claim 1 wherein the compound is 4-chloro-2-(4-chlorophenyl)quinazoline.

4. The fungicidal composition of claim 1, wherein the compound is 4-chloro-2-(4-tert-butylphenyl)quinazoline.

5. The fungicidal composition of claim 1 wherein the compound is 4-chloro-2-(2-thienyl)quinazoline.

6. A method of combating plant-infesting pathogenic fungi which comprises applying to the plants a fungicidally effective amount of a quinazoline of the formula:

wherein Ar is phenyl, thienyl or furyl; X is chlorine, bromine or mercapto radical; Y is halogen, alkyl of 1 to 4 carbons or alkoxy of 1 to 4 carbons; Z is alkyl of 1 to 4 carbons; and $m$ and $n$ are each 0 or 1.

7. The method of claim 6 wherein X is chlorine or bromine, Y is halogen or alkyl of 1 to 4 carbons, and $m$ is 0.

8. The method of claim 6 wherein the compound is 4-chloro-2-phenylquinazoline.

9. The method of claim 6 wherein the compound is 4-chloro-2-(4-methylphenyl)quinazoline.

10. The method of claim 6 wherein the compound is 4-chloro-2-(4-chlorophenyl)quinazoline.

11. The method of claim 6 wherein the compound is 4-chloro-2-(4-*tert*-butylphenyl)quinazoline.

12. The method of claim 6 wherein the compound is 4-chloro-2-(2-thienyl)quinazoline.

13. The method of claim 6 wherein the compound is 4-bromo-2-phenylquinazoline.

* * * * *